Figure 5:
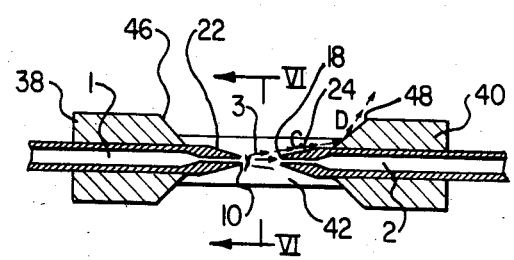

United States Patent [19]
Robinson et al.

[11] Patent Number: 4,598,578
[45] Date of Patent: Jul. 8, 1986

[54] FLUID DENSITY MEASURING APPARATUS

[75] Inventors: Barton R. Robinson; John W. Tanney, both of Nepean, Canada

[73] Assignee: Canadian Patents and Development Limited, Ottawa, Canada

[21] Appl. No.: 633,988

[22] Filed: Jul. 24, 1984

[30] Foreign Application Priority Data

Sep. 22, 1983 [CA] Canada ................................. 437291

[51] Int. Cl.⁴ .......................................... G01N 9/32
[52] U.S. Cl. .................. 73/32 R; 73/861.39
[58] Field of Search .............. 73/32 R, 37, 56, 30, 73/863.58, 861.18, 861.65, 861.39; 181/230, 233, 234, 235; 137/842

[56] References Cited

U.S. PATENT DOCUMENTS 3,595,258  7/1971  Kinner ................................ 137/842
3,783,676  1/1974  Tanney ............................. 73/32 R
3,864,971  2/1975  Tanney ........................... 73/861.39

Primary Examiner—Jerry W. Myracle
Assistant Examiner—Robert R. Raevis
Attorney, Agent, or Firm—Francis W. Lemon

[57] ABSTRACT

A fluid density measuring apparatus is provided of the kind wherein a nozzle directs a turbulent jet through another fluid to a receiver tube, and is improved in that surfaces, from which sound waves emanating directly from the jet will be reflected, are outside the jet flow and are inclined at obtuse angles to these sound waves so that they will be reflected away from the jet. The fluid from the jet may be the one whose density is to be measured, in which case the density of the other fluid is known. The inclined surfaces minimize any effect the reflected sound waves may have on the spreading rate of the jet from the nozzle and thus improve the sensitivity of the apparatus.

1 Claim, 9 Drawing Figures

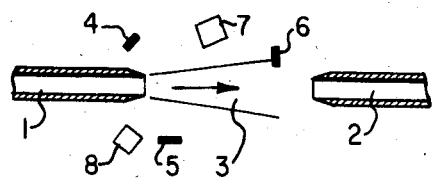
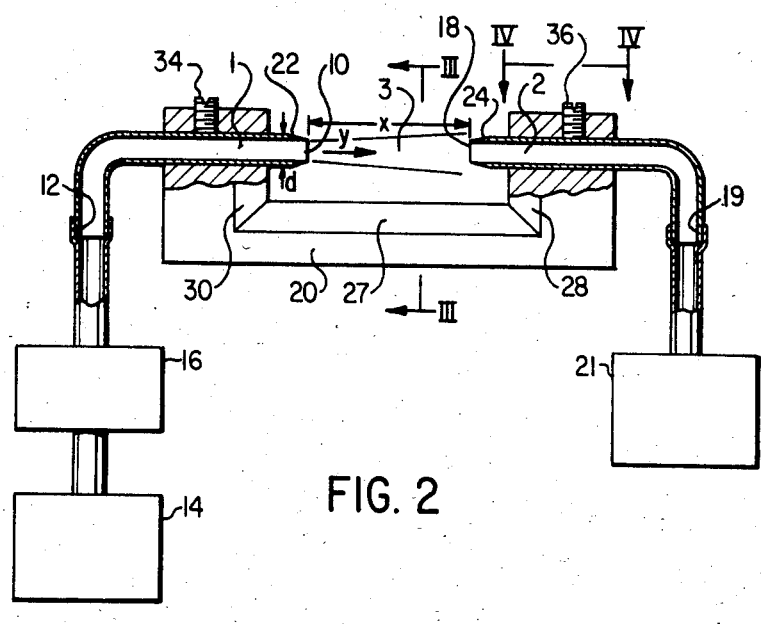
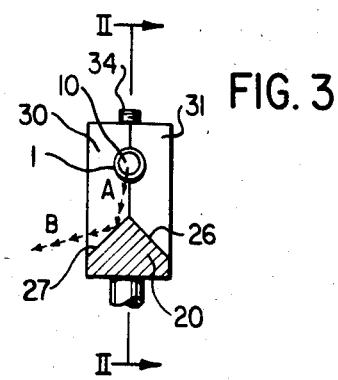
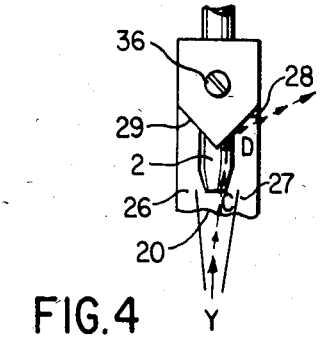
FIG. 1
FIG. 2
FIG. 3
FIG. 4

FLUID DENSITY MEASURING APPARATUS

This invention relates to a fluid density measuring apparatus.

It has already been proposed in U.S. Pat. No. 3,783,676, dated Jan. 8, 1974, "Method and Apparatus for Measuring The Density of a Fluid", J. W. Tanney, to provide a fluid densitometer comprising a nozzle and an open ended receiver facing the nozzle wherein a turbulent jet of fluid from the nozzle passes through the fluid substance whose density is to be measured and pressurizes the open end of the receiver. The pressure at the receiver depends upon the density of the fluid substance surrounding the jet and so that the density of that fluid substance may be determined by measuring the pressure at the receiver.

While this Tanney apparatus has proved to be useful, it has been found, in practice, that varying the density of the fluid, either in the jet or its surroundings, affects the sound wave pattern produced by the jet and also affects the attenuation or the spreading rate of the jet, thereby affecting the sensitivity of the jet to any jet produced sound wave reflected back into itself. This sensitivity to sound wave reflection may introduce an unpredictable variable into the performance of the apparatus.

There is a need for a densitometer of the type disclosed in the Tanney patent, wherein the effect of sound waves from the jet, on the jet spreading rate is minimized and, as a result, the sensitivity of the apparatus only to the density of fluid passing through the nozzle is improved.

According to the present invention there is provided a fluid substance density measuring apparatus comprising:

(a) a fluid jet forming device having a fluid jet orifice, (b) connecting means for connecting a pressurized fluid source to the device so that a first fluid may be delivered thereto, at substantially constant pressure, and cause a turbulent jet of fluid to issue from the orifice into a second fluid, (c) a receiver means having a receiver mouth facing the orifice, and spaced therefrom, to be pressurized by the dynamic pressure of the jet therefrom, and second fluid entrained therein, within the area bounded by the receiver mouth, (d) mounting means bridging the space between, and mounting the receiver means and the device so that the space between them is a turbulent jet forming space extending a distance of less than fifty times the maximum distance across the orifice, (e) connecting means for connecting the said receiver means to means for measuring the fluid pressure therein for providing an indication of the density of one of the first and second fluids when the density of the other one is known, and wherein the improvement comrpises, (f) substantially all of the surfaces of the fluid jet forming device, the receiver means and the mounting means, from which, in operation, sound waves emanating directly from the jet will be reflected "are outside the jet flow and", are each inclined at an obtuse angle with respect to all of the directions along which sound waves will flow from the jet towards that surface, so that these sound waves will be generally reflected by the inclined surfaces along paths away from the jet.

Figure 6:
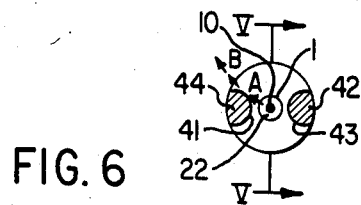
Figure 7:
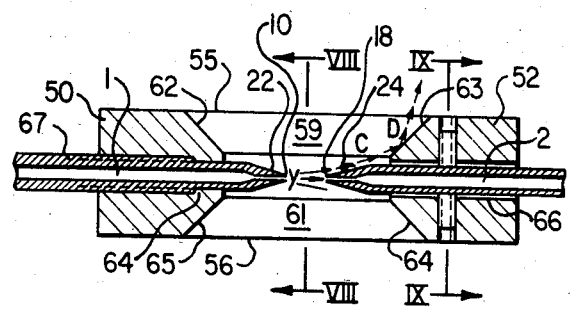
Figure 8:
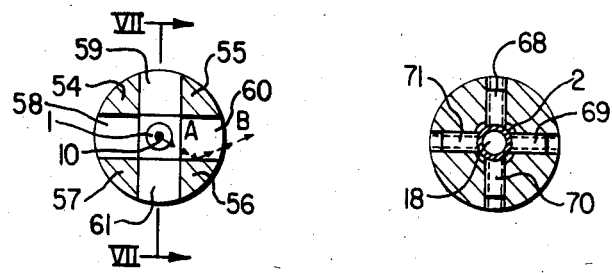
Figure 9:
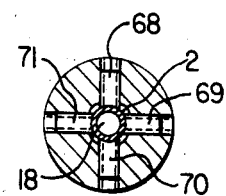

In the accompanying drawings which show apparatus used experimentally to verify the present invention and, by way of example, embodiments of the present invention, FIG. 1 is a diagrammatic, sectional side view of a nozzle and receiver of a fluid densitometer and the various positions at which sound reflectors were disposed to verify the present invention experimentally, FIG. 2 is a side view, partly sectional along II—II, FIG. 3, of fluid substance density measuring apparatus according to the present invention, FIG. 3 is a sectional end view along III—III, FIG. 2, FIG. 4 is a plan view along IV—IV, FIG. 2, of a portion of the apparatus shown in FIG. 2, FIG. 5 is a sectional side view along V—V, FIG. 6, of a different, fluid substance density measuring apparatus to that shown in FIGS. 2 to 4 but which is also according to the present invention, FIG. 6 is a sectional end view along VI—VI, FIG. 5, FIG. 7 is a sectional side view along VII—VII, FIG. 8, of yet another, different, fluid substance density measuring apparatus to that shown in FIGS. 2 to 4, or 5 to 7, but which is also according to the present invention, FIG. 8 is a sectional end view along VIII—VIII, FIG. 7, FIG. 9 is a sectional end view along IX—IX, FIG. 7.

The phenomena of sound wave generation by a jet and the effect of any sound waves reflected back into the jet as a result of this sound wave generation, is not fully understood but it can be demonstrated experimentally. This has been shown by David R. Glass in the American Institute for Aeronautics and Astronautics Journal, Vol. 6, No. 10, pp 1890-7, where an acoustic reflector and acoustic insulation were used to obtain "minimum" and "maximum" spreading rates in a turbulent supersonic jet. This phenomena can also be demonstrated with an unchoked turbulent jet to a lesser but still significant extent.

It has been shown that there is significant sound radiation from a subsonic turbulent jet at a Strouhal number of 0.25 to 0.30 as described by S. C. Crow and F. H. Champagne in the Journal of Fluid Mechanics, Vol. 48, Part 3, pp 547-91, where the Strouhal number $S = fd/u_o$ and where $f$ = frequency, $d$ = diameter of the nozzle and $u_o$ = velocity of the jet. It has been further shown by Y. V. Vaslov and A. S. Ginevski in National Aeronautics and Space Adminstration Technical Translation TT-F-15721 that excitation of a turbulent jet with sound at a jet Strouhal number of from 0.25 to 0.40 causes the maximum increase in the spreading rate of a jet. It can therefore be seen that a signficant sound wavelength generated by the jet is most effective in increasing the jet spreading rate when such a sound is reflected back into the jet.

Referring now to FIG. 1, the presence of the phenomena noted above was confirmed experimentally for the present invention by placing sound reflectors adjacent to a nozzle 1, jet 3, or receiver 2 in the form of tube, such as those shown designated 4 to 6. A reflector in the position of reflector 4, which is outside the jet flow, has been found to be most effective in increasing the spreading rate of the jet 3 and decreasing the total head or output pressure on the tube 2. A reflector in the position of reflector 5 has been found to have a lesser, but significant effect, on the spreading rate of the jet 3 and a reflector in the position of reflector 6, has been found to have a small, but significant effect, on the spreading rate of the jet 3. Elements of material that are sound reflecting, but which have only a sharp edge and no flat sides facing towards the core region of the jet, such as those designated 7 and 8, do not significantly affect the spreading rate of the jet 3.

Referring now to FIGS. 2 to 4, similar parts to those shown in FIG. 1 are designated by the same reference numerals and the previous description of them is relied upon to describe them.

In FIGS. 2 to 4 there is shown a fluid density measuring apparatus, comprising:

(a) a fluid jet forming device, in the form of nozzle 1, having a fluid jet orifice 10, (b) connecting means, in the form of a screw threaded end portion 12 of the nozzle 1, for connecting a pressurized fluid source 14 to the nozzle 1 so that a first fluid may be delivered thereto, at a substantially constant pressure by means of a pressure regulator 16, and cause a turbulent jet 3 of fluid to issue from the orifice 10 into a second fluid, (c) a receiver means, in the form of a tube 2, having a receiver mouth 18 facing the orifice 10, and spaced therefrom a distance X, to be pressurized by the dynamic pressure of the jet 3 therefrom, and second fluid entrained therein, within the area bounded by the receiver mouth 18, (d) mounting means, in the form of a 'C'-shaped bracket 20, bridging the space between and mounting the tube 2 and the nozzle 1 in the arms of the C-shape so that the space X between them is a turbulent jet 3 forming space extending a distance less than fifty times the maximum distance d across the orifice 10, (e) connecting means in the form of a screw threaded end portion 19 for connecting the tube 2 to device 21 for measuring the fluid pressure therein, for providing an indication of the density of the other one is known, and wherein the impovement comprises, (f) substantially all of the surfaces 22 of the nozzle 1, 24 of the tube 2, and 26 to 31 of the C-shaped bracket 20, from which, in operation, sound waves emanating directly from the jet will be reflected are outside the jet flow and, are each inclined at an obtuse angle with respect to the directions, such as a or c, along which sound waves will flow from the jet towards that surface, so that these sound waves will be generally reflected by the inclined surfaces 22, 24 and 26 to 31 along paths, such as b or d, away from the jet 3.

It should be noted that the inner surfaces 26 to 31 of the C-shaped bracket 20 are inclined towards each other in pairs to form knife edges between them, see FIGS. 3 and 4.

Two set screws 34 and 36 are provided to adjustably secure the nozzle 1 and tube 2, respectively, in the C-shaped bracket 20.

By inclining surfaces 22, 24 and 26 to 31 at obtuse angles, with respect to directions, such as a or c, so that sound waves will be reflected along paths, such as b or d, away from the jet 3, the reflection of jet generated sound waves back into the jet 3 is minimized and thus any effect on spreading rate of the jet 3 in this manner is minimized.

In this specification, a "turbulent, noise producing, jet" is defined, as is well understood by those skilled in the art, as having significant random or irregular flow velocity components as evidenced by the production of noise in contrast with a laminar jet where such irregularities are insignificant with no measurable noise being produced. (See McGraw-Hill, Encyclopedia of Science and Technology.)

In this specification "turbulent jet forming space" is defined as a space in which the turbulent jet is allowed to expand in a manner similar to the expansion of a turbulent jet in a volume which is unbounded at least to one side.

In one mode of operation, the apparatus is arranged as shown in FIGS. 2 to 4, with the nozzle 1 and tube 2 mounted in a second fluid whose density is to be measured, in this instance a gas. The apparatus was arranged with the distance "X" five times the minimum distance across the fluid jet orifice of the nozzle 1, which in this case was the diameter "d". A turbulent jet of air was directed, in the direction of arrow Y, as the first fluid whose density is known, from the nozzle 1 towards the tube 2.

The turbulent jet is defined in relation to FIG. 2 as being approximately conical in form when produced by a circular jet forming orifice and having a virtual origin on its axis approximately five diameters upstream of the plane of exit and the flow from the jet forming device and is clearly distinguished from what is known as laminar flow, in which the streamlines are essentially parallel, as described by Mott in U.S. Pat. No. 3,429,323, dated Feb. 25, 1969.

With the apparatus operating in the above manner, the pressure P given by the device 21 will depend upon the density of the second fluid surrounding the apparatus and thus the density of the second fluid may be determined from this measurement.

One reason for the pressure P varying with the second fluid density may be the variation of the spreading rate of the substantially unbounded turbulent jet with variations in the density of the second fluid in which it is submerged. With a given momentum at the jet orifice, the momentum at the receiver mouth is primarily dependent on the spreading rate of such turbulent jet. This phenomenon may be further complicated by the effect of concentration of the first fluid and the second fluid at the receiver mouth 18. Those effects are also dependent on orifice 10 to receiver mouth 18 spacing and to some extent on the supply pressure of the first fluid.

Tests were carried out to determine the sensitivity of the apparatus when used to measure various gas densities by supplying the nozzle 1 with air at various fixed pressures from the source 14 and with various spacings between the orifice 10 and the receiver mouth 18. In these tests the device 21 was capable of giving a maximum reading of eighty inches of mercury.

The results of these tests indicate that, with the apparatus used, an air supply pressure of the order of 60 inches mercury from the air supply 3 was the optimum value for a nozzle 1, to tube 2 spaicng "X" of 8.22 diameters. The reason for this is that with an air supply pressure of the order of 60 inches of mercury, the maximum change in pressure P in the tube 2 is obtained for a given range of densities of gas surrounding the apparatus, and so the sensitivity of the apparatus is greatest.

With the air supply pressure maintained at 60 inches of mercury the tests were continued using the same gases, but with the distance "X" between the nozzle 1 and the tube 22 set at different dimensions.

From the results it was found that with the apparatus used a nozzle 1 to tube 2 spacing of between eight to ten times "d", the nozzle diameter, provides the maximum sensitivity at 60 inches of mercury, air supply pressure. However, depending on the apparatus used, the spacing "X" may be up to 30 or even 50 times "d" and give useful results.

Using the apparatus as described, a nozzle 1 to tube 2 spacing "X" of 8.22 "d", the sensitivity of the apparatus is approximately 15 in. Hg output pressure difference for a density difference of 0.38 lb/cu.ft.

In a second mode of operation, the apparatus was again arranged as shown in FIGS. 2 to 4, but with the nozzle 1 and tube 2 mounted in a second fluid whose density was known while a turbulent jet of a first fluid whose density is to be measured was directed in the direction of arrow Y from the nozzle 1 towards the tube 2. Similar results were obtained as those given above for the first mode of operation.

In FIGS. 5 to 8 similar parts to those shown in FIGS. 1 to 4 are designated by the same reference numerals and the previous description is relied upon to describe them.

In FIGS. 5 and 6 a mounting means bridging the space between and mounting the nozzle 1 and tube 2 comprises two collars 38 and 40, mounting the nozzle 1 and tube 2, respectively, and two spacer rods 42 and 44 spacing the nozzle 1 and the tube 2.

The spacer rods 42 and 44 have curved surfaces 41 and 43, respectively, facing the jet 3 and the collars 38 and 40 have cone-shaped inner ends 46 and 48 to provide the inclined surfaces with respect to the general direction Y along which the jet 3 will flow.

The apparatus shown in FIGS. 5 and 6 operates in a similar manner to the apparatus shown in FIGS. 2 to 4.

In FIGS. 7 to 9 the mounting means bridging the space between the mounting means bridging the space between and mounting the tube 2 and the nozzle 1 comprises two collars 50 and 52 integral with four spacer arms 54 to 57. As shown in FIG. 8, the arms 54 to 57 are sectorial in cross-section to provide passages 58 to 61 therebetween for gas to enter, and the collars 50 and 52 are provided with inclined surfaces, such as inclined surfaces 62 to 65, at the ends of the passages 58 to 61.

The nozzle 1 is secured in the collar 50 by means of a screw thread portion 67 being screwed into a corresponding screw thread in the collar 50 until the nozzle 1 is located in and against a stepped portion 64 in the collar 50.

The tube 2 is secured in a loosely fitting bore 66 in the collar 52 by four set screws 68 to 71 by which the tube 2 can be aligned with and spaced from the nozzle 1.

The apparatus shown in FIGS. 7 to 9 operates in a similar manner to the apparatus shown in FIGS. 2 to 4.

We claim:

1. A fluid substance density measuring apparatus, comprising:
   (a) a fluid jet forming device having fluid jet orifice;
   (b) connecting means for connecting a pressurized fluid source to the device so that a first fluid may be delivered thereto, at substantially constant pressure, and cause a turbulent jet of fluid to issue from the orifice into a second fluid;
   (c) a receiver means having a mouth facing the orifice, and spaced therefrom, to be pressurized by the dynamic pressure of the jet therefrom, and second fluid entrained therein, within the area bounded by the receiver mouth;
   (d) mounting means bridging the space between and mounting the receiver means and the device so that the space between them is a turbulent jet forming space extending a distance of less than fifty times the maximum distance across the orifice;
   (e) connecting means for connecting the said receiver means to means for measuring the fluid pressure therein, for providing an indication of the density of one of the first and second fluids when the density of the other one is known;
   (f) substantially all of the surfaces of the fluid jet forming device, the receiver means and the mounting means, from which, in operation, sound waves emanating directly from the jet will be reflected, are outside the jet flow and are each inclined at an obtuse angle with respect to all of the directions along which sound waves will flow from the jet towards that surface, so that these sound waves will be generally reflected by the inclined surfaces along paths away from the jet; and
   (g) the mounting means comprises two collars, with one collar mounting the receiver means and the other collar mounting the device, and two semi-circular spacer rods spacing the nozzle and the receiver means, the spacer rods have curved surfaces and the collars have cone shaped inner ends to provide the inclined surfaces with respect to the general direction along which the jet will flow.

* * * * *